(12) United States Patent
Buchbinder et al.

(10) Patent No.: US 9,150,485 B2
(45) Date of Patent: *Oct. 6, 2015

(54) PROCESS FOR CONTROLLING REACTION AND CRYSTALLIZATION SOLVENT COMPOSITION IN PROCESS FOR PRODUCTION OF AROMATIC CARBOXYLIC ACID

(71) Applicant: UOP LLC, Des Plaines, IL (US)

(72) Inventors: Avram M. Buchbinder, Chicago, IL (US); Raymond Shih, Elgin, IL (US); Alakananda Bhattacharyya, Glen Ellyn, IL (US); Evan B. Jorgenson, Mt. Prospect, IL (US); Tatsamai Jarusiripipat, Chicago, IL (US); Nina Kuznetsova, Novosibirsk (RU)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/048,569

(22) Filed: Oct. 8, 2013

(65) Prior Publication Data

US 2015/0099897 A1  Apr. 9, 2015

(51) Int. Cl.
*C07C 51/29* (2006.01)

(52) U.S. Cl.
CPC ..................... *C07C 51/29* (2013.01)

(58) Field of Classification Search
CPC ....................................... C07C 51/29
See application file for complete search history.

(56) References Cited

U.S. PATENT DOCUMENTS

| 2,723,995 | A | 11/1955 | Rutherford |
| 2,826,607 | A * | 3/1958 | Toland, Jr. ............... 562/483 |
| 4,914,230 | A | 4/1990 | Abrams |
| 7,094,925 | B2 | 8/2006 | Earle et al. |
| 7,625,941 | B2 | 12/2009 | Harmer et al. |
| 7,985,875 | B2 | 7/2011 | Hashmi et al. |
| 2007/0010688 | A1 | 1/2007 | Ko et al. |
| 2007/0129568 | A1 | 6/2007 | Flanagan et al. |
| 2012/0004449 | A1 | 1/2012 | Bhattacharyya et al. |
| 2012/0004450 | A1 | 1/2012 | Bhattacharyya et al. |
| 2012/0004454 | A1 | 1/2012 | Bhattacharyya et al. |
| 2012/0004455 | A1 | 1/2012 | Bhattacharyya et al. |
| 2012/0004456 | A1 | 1/2012 | Bhattacharyya |
| 2013/0041175 | A1 | 2/2013 | Bhattacharyya et al. |

FOREIGN PATENT DOCUMENTS

| WO | WO 2012/066296 | 5/2012 |
| WO | 2013101331 A1 | 4/2013 |

OTHER PUBLICATIONS

PCT International Search Report for PCT/IS2014/057679, mailing date Oct. 29, 2014.

* cited by examiner

*Primary Examiner* — Yong Chu
*Assistant Examiner* — Ana Z Muresan (57) ABSTRACT

Processes have been developed for oxidizing alkyl aromatic compounds, and which reduce the amount of 4-CBA in the solid oxidation products. The process can reduce the makeup amount of ionic liquid, carboxylic acid, catalyst, bromine source, and ammonia source.

20 Claims, 3 Drawing Sheets

PROCESS FOR CONTROLLING REACTION AND CRYSTALLIZATION SOLVENT COMPOSITION IN PROCESS FOR PRODUCTION OF AROMATIC CARBOXYLIC ACID

JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are 1) UOP LLC and 2) Boreskov Institute of Catalysis.

BACKGROUND OF THE INVENTION

Oxidation of alkyl aromatic compounds, e.g., toluene and xylenes, are important commercial processes. A variety of oxidation products may be obtained including aromatic carboxylic acids such as terephthalic acid (1,4-benzenedicarboxylic acid) and isophthalic acid (1,3-benzenedicarboxylic acid) which are used, for example, in the polymer industry.

It is known that oxidation products, such as aromatic alcohols, aromatic aldehydes, aromatic ketones, and aromatic carboxylic acids, may solidify or crystallize at oxidation conditions and/or as the reaction mixture cools. Thus, mixtures of oxidation products may be produced which require further processing to increase the purity of the desired product. For example, in the production of terephthalic acid, the oxidation product is often referred to as crude terephthalic acid because it contains impurities including color bodies and intermediate oxidation products, especially 4-carboxybenzaldehyde (4-CBA). To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. Often several purification steps are used.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidizing in the presence of acetic acid as a solvent, a cobalt salt as a catalyst, and an initiator. The oxidation step is followed by flashing the reaction mixture to remove volatile substances and cooling and filtering the material to get crude benzene di-carboxylic acid as a solid product and a filtrate. Recrystallizing the crude benzene di-carboxylic acid to obtain at least 99% purity and recycling of the filtrate are also disclosed.

U.S. Pat. No. 7,094,925 discloses a process for preparing an alkyl-aromatic compound. The process includes mixing an oxidizing agent or sulfur compound in the presence of an ionic liquid. Air, dioxygen, peroxide, superoxide, or any other form of active oxygen, nitrite, nitrate, and nitric acid or other oxides or oxyhalides of nitrogen (hydrate or anhydrous) can be used as the oxidizing agent. The process is typically carried out under Brønsted acidic conditions. The oxidation is preferably performed in an ionic liquid containing an acid promoter, such as methanesulfonic acid. The product is preferably a carboxylic acid or ketone or intermediate compound in the oxidation, such as an aldehyde, or alcohol.

U.S. Pat. No. 7,985,875 describes a process for preparing an aromatic polycarboxylic acid by liquid phase oxidation of a di- or tri-substituted benzene or naphthalene compound. The process involves contacting the aromatic compound with an oxidant in the presence of a carboxylic acid solvent, a metal catalyst, and a promoter in a reaction zone. The promoter is an ionic liquid comprising an organic cation and a bromide or iodide anion. The promoter is used in a concentration range of about 10 to about 50,000 ppm (based on solvent) with a preferred range of 10-1,000 ppm. No other promoters, such as bromine-containing compounds, need to be used in the process. The process produces crude terephthalic acid (CTA) having 1.4-2.2% 4-CBA. Purification of the CTA is required to obtain purified terephthalic acid (PTA).

US 2010/0174111 describes a process for purifying aryl carboxylic acids, such as terephthalic acid. The impure acid is dissolved or dispersed in an ionic liquid. A non-solvent (defined as a molecular solvent for which the ionic solvent has high solubility and for which the aryl carboxylic acid has little or no solubility) is added to the solution to precipitate the purified acid.

U.S. Pat. No. 7,692,036, 2007/0155985, 2007/0208193, and 2010/0200804 disclose a process and apparatus for carrying out the liquid-phase oxidation of an oxidizable compound. The liquid phase oxidation is carried out in a bubble column reactor that provides for a highly efficient reaction at relatively low temperatures. When the oxidized compound is para-xylene, the product from the oxidation reaction is CTA which must be purified. Purification is said to be easier than for conventional high temperature processes.

Recently, a method was disclosed to utilize a solvent comprising ionic liquid which significantly reduces the amount of 4-CBA in products. For example, US 2012/0004449, 2012/0004450, 2012/0004454, each of which is incorporated herein by reference, describe processes and mixtures for oxidizing alkyl aromatic compounds. The process involves forming a mixture comprising the alkyl-aromatic compound, a solvent, a bromine source, and a catalyst, and contacting the mixture with an oxidizing agent at oxidizing conditions to produce an oxidation product comprising at least one of an aromatic aldehyde, and aromatic alcohol, an aromatic ketone, and an aromatic carboxylic acid. The solvent comprises a carboxylic acid having one to seven carbon atoms and an ionic liquid selected from an imidazolium ionic liquid, a pyridinium ionic liquid, a phosphonium ionic liquid, a tetra alkyl ammonium ionic liquid, or combinations thereof.

US 2012/0004456, which is incorporated herein by reference, describes a process for purifying crude terephthalic acid with a solvent comprising an ionic liquid at purifying conditions to produce a solid terephthalic acid product having a concentration of contaminant lower than the first concentration.

Ideally, the ionic liquid and other solvent components would be recycled in order to avoid the cost of adding large amounts of fresh material to the process. The recycle process needs to take into account changes to the ionic liquid mixture composition over time.

There is a need for solvent recycle processes in the oxidation of alkyl aromatic compounds to aromatic carboxylic acids.

SUMMARY OF THE INVENTION

One aspect of the invention is a process for oxidizing an alkyl aromatic compound. In one embodiment, the process includes contacting the alkyl aromatic compound, a first solvent comprising an ionic liquid and a carboxylic acid, a bromine source, a catalyst, and an oxidizing agent in a reaction zone under oxidizing conditions to produce an oxidation product comprising aromatic carboxylic acid, and at least one of dissolved unoxidized alkyl aromatic compound or dissolved partially oxidized alkyl aromatic compound, at least 25% of the aromatic carboxylic acid remaining in solution. At least a portion of the aromatic carboxylic acid in the first crystallization zone is crystallized to produce a solid product comprising a crystallized aromatic carboxylic acid and a mother liquor liquid comprising the first solvent, and the at least one of unoxidized alkyl aromatic compound or partially oxidized alkyl aromatic compound and optionally aromatic carboxylic acid in solution. The solid product is separated from the mother liquor liquid. Optionally one or more of additional ionic liquid, additional carboxylic acid, additional bromine source, or additional ammonia or ammonium compound is introduced into the mother liquor liquid. At least a portion of the mother liquor liquid is recycled to the first reaction zone.

In some embodiments, the mother liquor liquid is separated into a volatile portion comprising one or more of the carboxylic acid, the crystallization solvent, the bromine source, and water, and a nonvolatile portion comprising the ionic liquid, the catalyst, and the at least one of dissolved unoxidized alkyl aromatic compound or dissolved partially oxidized alkyl aromatic compound. One or more of additional ionic liquid, additional carboxylic acid, or additional bromine source is introduced into the nonvolatile portion.

In some embodiments, the oxidation product further comprises an amide compound, and the process further comprises hydrolyzing the amide compound with a second carboxylic acid, water, or both to an ammonium compound, or ammonia, and an aromatic carboxylic acid.

In some embodiments, the mother liquor liquid is divided into a first portion and a second portion. The first portion is recycled to the reaction zone, and the second portion is separated into a volatile portion comprising one or more of the carboxylic acid, the bromine source, and water, and a nonvolatile portion comprising the ionic liquid, the catalyst, and the at least one of dissolved unoxidized alkyl aromatic compound or dissolved partially oxidized alkyl aromatic compound.

DETAILED DESCRIPTION OF THE INVENTION

Processes for recycling solvent components in oxidation processes for alkyl aromatic compounds utilizing ionic liquids have to address the possibility that the solvent composition will change over time. For example, volatile components, such as acetic acid, may be depleted due to volatility or reaction. Other components, such as ionic liquid, may react and change their chemical form, as discussed in co-pending application Ser. No. 14/039,703, entitled ACTIVE IONIC LIQUID MIXTURES FOR OXIDIZING ALKYLAROMATIC COMPOUNDS, filed Sep. 27, 2013, which is incorporated herein by reference. Still other components, such as dissolved reaction intermediates and products, will accumulate in the liquid phase.

Part of the advantage of utilizing ionic liquid solvents arises from the solubility of the aromatic carboxylic acid product, such as terephthalic acid, in the medium. High terephthalic acid solubility leads to less crystallization during the oxidation reaction, which allows for more complete conversion of the intermediates before they co-crystallize into terephthalic acid crystals, reducing the impurity levels of the product.

While high solubility provides an advantage from the standpoint of low impurity levels, a different approach may be needed for crystallization, such as adding carboxylic acid (e.g., acetic acid), or water. Also, some compositions of oxidation media may comprise ammonium acetate, ammonia, or another ammonia source. In the presence of ammonium acetate, a portion of the aromatic carboxylic acids reacts to form amide derivatives of aromatic carboxylic acids. The addition of water and/or a carboxylic acid such as acetic acid hydrolyzes these compounds to reform the corresponding aromatic carboxylic acid. The simple recycling of the ionic liquid solvent, as described in U.S. application Ser. No. 13/715,620, entitled IONIC LIQUID OXIDATION AND CRYSTALLIZATION PROCESS FOR TEREPHTHALIC ACID PRODUCTION, filed Dec. 14, 2012, which is incorporated herein by reference, is not practically compatible with the addition of carboxylic acid and/or water as a crystallization solvent because significant amounts of fresh solvent would need to be added to the recycle stream to dilute the recycled mother liquor which would contain significant amounts of crystallization solvent.

In order to control reaction rates and selectivity, maintaining the proper balance of the components in the solvent mixture is desirable. The recycle process needs to include a mechanism to maintain an active composition. For example, the formation of amides during the reaction if ammonia or ammonium compounds are present depletes the ammonia concentration and, in some examples, leads to high impurity levels if the mother liquor is recycled without adding additional ammonia. In addition, the ratio of ionic liquid to carboxylic acid in the solvent mixture can also affect the level of impurities.

U.S. application Ser. No. 13/715,620, and US Publication No. 2013/0041175, which are incorporated herein by reference, describe oxidation and crystallization processes of alkyl aromatic compounds that include recycle of a stream containing used ionic liquid solvent mixtures, unreacted intermediates, and dissolved aromatic carboxylic acids products. US 2012/0004449, 2012/0004450, 2012/0004454 and US 2012/0004456 describe solvent mixtures comprising ionic liquid and carboxylic acids used in the oxidation of alkyl aromatic compounds, and the purification of terephthalic acid. These applications demonstrate that the composition of the reaction products, including the level of 4-CBA, and the extent of conversion of the toluic acid intermediate are strongly dependent on the solvent composition. The active composition of the ionic liquid portion of the mixture and methods of obtaining the active composition are described in pending Application Serial No. PCT/US14/53507, entitled ACTIVE IONIC LIQUID MIXTURES FOR OXIDIZING ALKYLAROMATIC COMPOUNDS, filed Aug. 28, 2014.

Processes have been developed to obtain recycle ionic liquid streams which are active for oxidation of alkyl aromatic compounds, and which reduce the amount of 4-CBA in the solid products. The process can reduce operating costs by reducing the makeup amount of ionic liquid, carboxylic acid, catalyst, bromine source, and ammonia source. It can also decrease the residence time required for the reaction. This can be done by removing volatile components, including carboxylic acid, such as acetic acid, and water, and solid components, such as aromatic carboxylic acids and other crystallized products, and then adding the proper proportion of fresh or recycled carboxylic acid, water, and ammonia source or other base. Alternatively, all or most of the recycled mother liquor can be recycled and its composition and properties adjusted by adding makeup components.

Additionally, the ammonia source, such as ammonium acetate, and carboxylic acid components, such as acetic acid, can be recycled. If an ammonia source is included in the reaction, amides can be formed. If the aromatic carboxylic acid is terephthalic acid, amides of terephthalic acid (terephthalic acid monoamide) and toluic acid (toluamide) are formed. Ammonia can be recovered from hydrolysis of these amides and recycled.

Residence time can be reduced by running at lower conversion and recycling the un-reacted intermediates because of the high solubility of the aromatic carboxylic acids in ionic liquid. Recycling a portion of the solvent and dissolved species can be utilized to minimize the extent of co-crystallization of intermediates such as 4-CBA and toluic acid. The reaction can be run with low aromatic carboxylic acid concentration in the reactor and not result in co-crystallization of intermediates because all of the components remain in the liquid phase at the reaction conditions.

The oxidation generates liquid products, solid products, and dissolved solid products. The amount of each depends on the temperature and the composition of the solvent and product, but there is generally more terephthalic acid dissolved in the liquid portion when using mixtures containing ionic liquid compared to mixtures containing only a carboxylic acid (see Example 3). Oxidation is generally followed by a crystallization step or other separation step. In the crystallization step, the temperature is reduced, or the solvent composition is changed to be less favorable for dissolution of the solid products, or both. Crystallization by changing the solvent composition can be accomplished by adding a solvent such as acetic acid or water in which terephthalic acid is less soluble than in the reaction solvent. Crystallization is followed by separation of solid and liquid products. The liquid portion is subjected to treatments for recycle.

The process can be used for the oxidation of alkyl aromatic compounds to aromatic carboxylic acids. Suitable alkyl aromatic compounds or feeds to be oxidized include aromatic compounds comprising at least one benzene ring having at least one alkyl group. Methyl, ethyl, and isopropyl alkyl groups are preferred alkyl groups, although other alkyl groups can be used if desired. In an embodiment, the alkyl aromatic compound is selected from toluene, para-xylene, ortho-xylene, and meta-xylene. The feed may comprise more than one alkyl aromatic compound. As the oxidation reaction generally proceeds through successive degrees of oxidization, suitable feed compounds also include partially oxidized intermediates relative to the desired oxidized product. For example, in the production of terephthalic acid, the alkyl aromatic feed may include para-toluic acid and/or 4-carboxybenzaldehyde (4-CBA). For ease of discussion, the oxidation of para-xylene to terephthalic acid with acetic acid as the carboxylic acid will be described. However, it will be understood by those of skill in the art that other alkyl aromatic compounds and carboxylic acids could be used.

Figure 1:
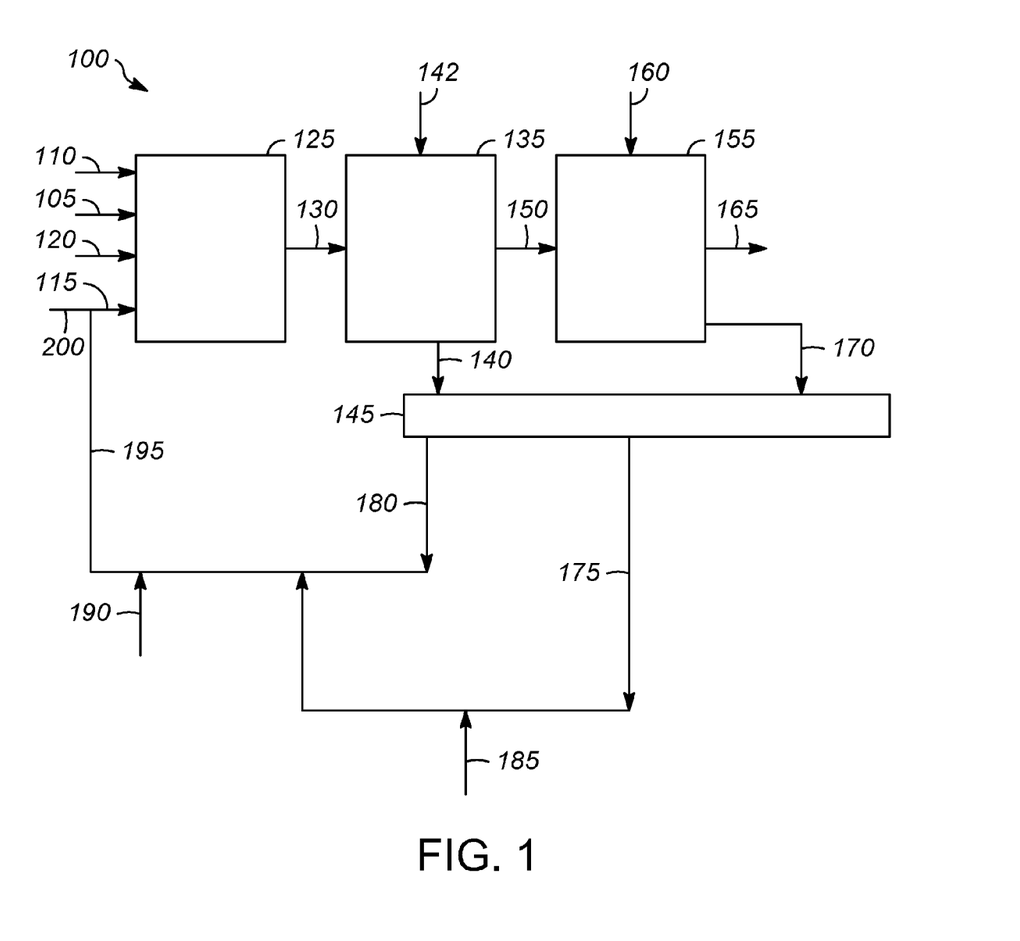
FIG. 1 is an illustration of one embodiment of an oxidation process to produce aromatic carboxylic acids including solvent recycle.

One embodiment of a recycle process 100 is shown in FIG. 1. Para-xylene 105, and oxidant 110, such as air, solvent 115, and optionally ammonia or an ammonium source 120 are introduced into oxidation reaction zone 125 where the paraxylene 105 is oxidized to terephthalic acid.

In some embodiments, the solvent comprises at least one ionic liquid. Two or more ionic liquids can be used, if desired.

Generally, ionic liquids are non-aqueous, organic salts composed of ions where the positive ion is charge balanced with a negative ion. These materials have low melting points, often below 100° C., undetectable vapor pressure, and good chemical and thermal stability. The cationic charge of the salt is localized over hetero atoms, and the anions may be any inorganic, organic, or organometallic species.

In an embodiment, ionic liquids suitable for use include, but are not limited to, one or more of imidazolium ionic liquids, pyridinium ionic liquids, tetra alkyl ammonium ionic liquids, and phosphonium ionic liquids. More than one ionic liquid may be used. Imidazolium, pyridinium, and ammonium ionic liquids have a cation comprising at least one nitrogen atom. Phosphonium ionic liquids have a cation comprising at least one phosphorus atom. In an embodiment, the ionic liquid comprises a cation selected from alkyl imidazolium, di-alkyl imidazolium, and combinations thereof. In another embodiment, the ionic liquid comprises an anion selected from halides, acetate, carboxylates, and combinations thereof. The ionic liquid may comprise at least one of 1-butyl-3-methylimidazolium acetate (BMImOAc), 1-butyl-3-methylimidazolium bromide (BMImBr), 1-hexyl-3-methylimidazolium acetate (C6MImOAc), and 1-hexyl-3-methylimidazolium bromide (C6MImBr).

The ionic liquid can be provided, or it can be generated in situ from appropriate precursors, or both.

The mode of introducing the ionic liquid precursors may vary depending on the nature of the alkyl aromatics being oxidized and the nature and purity of the product desired. In one mode of addition, the cation precursors and the anion precursors (generally liquids at room temperature and pressure) are mixed with a carboxylic acid (for example, acetic acid) solvent and introduced into the oxidation reactor(s). In another mode of addition, the ionic liquid precursors may be mixed with the alkyl aromatic feed and introduced into the oxidation reactors. In another mode of addition, both cation and anion ionic liquid precursor components may be introduced into the bottom of the reactor without pre-mixing with any other oxidation reactor components such as the feed, carboxylic acid solvent, and catalyst package.

The solvent can also comprise a carboxylic acid. When carboxylic acids are used in the solvent, the amount of carboxylic acid is decreased compared with conventional processes in order to avoid excessive solvent volumes. The carboxylic acid desirably has from 1 to 7 carbon atoms. In an embodiment, the carboxylic acid comprises acetic acid. The solvent may contain more than one carboxylic acid. For example, the solvent may further comprise benzoic acid. In another embodiment, the carboxylic acid of the solvent is acetic acid.

In an embodiment, the solvent has a ratio of the ionic liquid solvent to the carboxylic acid solvent within a range of about 0.1:1 to about 10:1 by weight, or about 0.1:1 to about 7:1, or about 0.1:1 to about 5:1, or about 0.1:1 to about 3:1. The amount of ionic liquid includes ionic liquid precursors, if present. The optional ionic solid or material capable of forming an ionic salt in solution discussed below, if present, is included in the amount of ionic liquid.

Optionally, an ionic solid, such as ammonium acetate ($NH_4OAc$) and/or ammonium bromide ($NH_4Br$), can be added to the mixture. Alternatively, a material which is capable of forming an ionic salt in solution can be added. The material can form the ionic salt in solution by combining with ions present in the solution. For example, in a solution containing bromide (for example in the form of HBr) or acetate ions (for example, in the form of acetic acid), ammonia could combine with the bromide or acetate ions forming ammonium bromide or ammonium acetate. The use of one or more ionic solids or materials capable of forming an ionic salt in solution provided an additional reduction in the level of impurities.

In an embodiment, the amount of ionic solid and material capable of forming an ionic salt in solution ranges from about 0.5 wt % to about 35 wt %, relative to the weight of the solvent, or from about 10 wt % to about 30 wt %, relative to the weight of the solvent. The solvent includes the carboxylic acid, the ionic liquid and/or ionic liquid precursors, the optional ionic solid or material capable of forming an ionic salt in solution, the optional water.

Optionally, the solvent may further comprise water. The water may be added to the mixture or generated in the mixture during the oxidation process.

In an embodiment, the ratio of solvent to alkyl-aromatic compound in the mixture ranges from about 1.5:1 to about 25:1 by weight, or from about 3:1 to about 10:1 by weight, or from about 4:1 to about 6:1 by weight. The solvent includes the carboxylic acid, the ionic liquid and/or ionic liquid precursor, the optional ionic solid or material capable of forming an ionic salt in solution, the optional water.

The catalyst comprises at least one of cobalt, manganese, titanium, chromium, copper, nickel, vanadium, iron, molybdenum, tin, cerium and zirconium. In an embodiment, the catalyst comprises cobalt and manganese. The metal may be in the form of an inorganic or organic salt. For example, the metal catalyst may be in the form of a carboxylic acid salt, such as, metal acetate and hydrates thereof. Exemplary catalysts include cobalt (II) acetate tetrahydrate and manganese (II) acetate, individually or in combination. In an embodiment, the amount of manganese (II) acetate is less than the amount of cobalt (II) acetate tetrahydrate by weight.

The amount of catalyst used in the invention may vary widely. For example, the amount of cobalt may range from about 0.001 wt % to about 2 wt % relative to the weight of the solvent. In an embodiment, the amount of cobalt ranges from about 0.05 wt % to about 2 wt % relative to the weight of the solvent. The amount of manganese may range from about 0.001 wt % to about 2 wt % relative to the weight of the solvent. In an embodiment, the amount of manganese ranges from about 0.05 wt % to about 2 wt % relative to the weight of the solvent. In another embodiment, the ratio of cobalt to manganese ranges from about 3:1 to about 1:2 by weight on an elemental metal basis.

Bromine sources are generally recognized in the art as being catalyst promoters and include bromine, ionic bromine, e.g. HBr, NaBr, KBr, $NH_4Br$; and/or organic bromides which are known to provide bromide ions at the oxidation conditions, such as, benzylbromide, mono and di-bromoacetic acid, bromoacetyl bromide, tetrabromoethane, ethylene dibromide. In an embodiment, the bromine source comprises or consists essentially of or consists of hydrogen bromide. The amount of hydrogen bromide may range from about 0.01 wt % to about 5 wt %, relative to the weight of the solvent, or about 0.01 wt % to about 4 wt %, or about 0.01 wt % to about 3 wt %, or about 0.01 wt % to about 2 wt %, or about 0.01 wt % to about 1.5 wt %, or about 0.01 wt % to about 1 wt %. In another embodiment, the amount of hydrogen bromide ranges from about 0.25 wt % to about 0.75 wt %, relative to the weight of the solvent. The solvent includes the carboxylic acid, the ionic liquid, the ionic liquid precursors, the optional ionic solid or material capable of forming an ionic salt in solution, and the optional water.

Suitable oxidizing agents for the process provide a source of oxygen atoms to oxidize the p-xylene and/or p-toluic acid, and/or another intermediate oxidization product at the oxidation conditions employed. Examples of oxidizing agents include peroxides, superoxides, and nitrogen compounds containing oxygen such as nitric acids. In an embodiment, the oxidizing agent is a gas comprising oxygen, e.g. air, and molecular oxygen. The gas may be a mixture of gases. The amount of oxygen used in the process is preferably in excess of the stoichiometric amount required for the desired oxidation process. In an embodiment, the amount of oxygen contacted with the mixture ranges from about 1.2 times the stoichiometric amount to about 100 times the stoichiometric amount. Optionally, the amount of oxygen contacted with the mixture may range from about 2 times the stoichiometric amount to about 30 times the stoichiometric amount.

At least a portion of the components provides a liquid phase, although dissolution of one or more of the mixture components may not be complete at any, or some, time during the process. The liquid phase may be formed by mixing the components at ambient conditions. In another embodiment, the liquid phase is formed as the temperature of the mixture is raised, e.g., to about 100° C. to about 240° C. A mixture of the components may be formed prior to the oxidation step, in the same or different vessel as that used in the oxidation step. In another embodiment, a mixture of the components is formed in an oxidation reactor, e.g. adding various streams of the components individually and/or in combination to a continuous or semi-continuous oxidation reactor. The combined components and/or various streams of the components may be heated before they are mixed together or mixed before they are heated, as desired.

Though many conventional alkyl aromatic oxidation processes are typically conducted in a mixed phase, and often include three phases (e.g. solid, gas, and liquid), they are frequently referred to in the art as "liquid phase" oxidation processes because the oxidation conditions are maintained to provide at least a portion of the mixture in the liquid phase. It is also known in the art that the number of phases present may vary over time during the process. Processes according to the instant invention may also be conducted in a liquid phase or mixed phase in a similar manner as known in the art.

Conventional, liquid phase oxidation reactors as known in the art may be used to practice the invention. Examples include vessels, which may have one or more mechanical agitators, and various bubble column reactors such as those described in U.S. Pat. No. 7,692,036. It is also known to design, operate, and control such reactors and the oxidation reaction for the oxidation conditions employed including, e.g., the temperature, pressure, liquid and gas volumes, and corrosive nature of the liquid and gas phases where applicable. See, e.g. U.S. Pat. No. 7,692,036 and U.S. Pat. No. 6,137,001.

The oxidation temperature, pressure and residence time may vary based on a variety of factors including for example, the reactor configuration, size, and whether the process is batch, continuous, or semi-continuous. An oxidation condition may also vary based on other oxidation conditions. For example, use of a particular temperature range may enable use of a different residence time range.

Oxidation reaction zone 125 is typically operated at a temperature of about 240° C. or less, or in a range of about 170° C. to about 240° C., or about 190° C. to about 220° C. The pressure is generally in a range of about 0.69 MPa(g) (100 psig) to about 4.1 MPa(g) (600 psig), or about 1.4 MPa(g) (200 psig) to about 2.8 MPa(g) (405 psig).

The residence time is controlled to allow limited terephthalic acid conversion and crystallization in order to adjust the final product quality. The residence time is generally less than 180 min, or less than 90 min, or less than 60 min, or less than 45 min, or less than 30 min.

The effluent 130 from the oxidation zone 125 is sent to a first crystallization zone 135. Due to the relatively high solubility of terephthalic acid in ionic liquid, a significant portion of the terephthalic acid product is dissolved in the liquid at the reaction temperature. The effluent 130 contains less than 80% precipitated terephthalic acid, or less than 50% or less than 40%, or less than 30%, or less than 20%, or less than 15%, or less than 10%, or less than 5%. Because of the high solubility, crystallization is necessary to recover the product. Additionally, the product contains amides if ammonia or ammonium acetate is used in the reactor. Crystallization is initiated by lowering the temperature in the first crystallization zone 135. The temperature of the first crystallization zone 135 is generally at least 10° C., or at least 20° C. less than the temperature of the oxidation zone 125. The first crystallization zone 135 is generally at a temperature of about 220° C. or less, or about 150° C. to about 220° C., or about 170° C. to about 220° C., or about 180° C. to about 200° C. The pressure is generally in a range of about 0 MPa(g) (0 psig) to about 2.1 MPa(g) (300 psig), or 0 MPa(g) (0 psig) to about 2.8 MPa(g) (400 psig).

Alternatively, crystallization is initiated by first adding a crystallization solvent 142 in the first crystallization zone 135. The crystallization solvent is a solvent in which the terephthalic acid product has a lower solubility compared to the oxidation solvent. Examples of crystallization solvents include water and acetic acid. Addition of the crystallization solvent 142 can take place before, after, or in place of, reducing the temperature.

If the product contains amides, the crystallization solvent can also serve as a hydrolyzing solvent if the crystallization solvent comprises water and/or an acid. In such a case where the product contains amides, crystallization should not be completed by reducing the temperature before adding a hydrolyzing solvent because amide products may crystallize with the desired aromatic acid products, and an additional re-crystallization would be required to recover terephthalic acid.

During or after this crystallization step, some of the liquid portion 140 can be removed, if desired. The liquid portion 140 can be directed to the volatiles separation zone 145, where the liquid portion with dissolved solids 140 is separated into a volatile portion 175 and a non-volatile portion 180. The volatiles separation zone 145 may or may not be the same vessel as one of the crystallization zones 135 or 155. Volatiles separation can be performed by one or more of distillation, evaporation, flash evaporation (achieved by reducing pressure), centrifugation or other separation step which removes the volatile portion of the liquid. The volatile portion 175 includes acetic acid, hydrobromic acid, water, and optionally ammonia, as well as methyl acetate and any other volatile side products that are generated in the oxidation. The non-volatile portion 180 includes ionic liquid, cobalt and manganese catalyst, dissolved reaction intermediates and products (which include toluic acid, toluamide, 4-CBA, terephthalic acid, and terephthalic acid monoamide).

Additional oxidation can also occur in the first crystallization zone 135, if desired.

After lowering the temperature to initiate crystallization in the first crystallization zone 135, the effluent 150 from the first crystallization zone 135 is sent to a second crystallization zone 155 where a second crystallization solvent 160 is added. The second crystallization solvent can be the same as the first crystallization solvent, or it can be different.

The use of the second crystallization solvent 160 in the second crystallization zone can be in addition to, or it can replace, lowering the temperature in the first crystallization zone 135, and/or adding the crystallization solvent 142 in the first crystallization zone 135. The temperature of the second crystallization zone 155 is generally at least 10° C., or at least 20° C. less, than the temperature of the first crystallization zone 135. The second crystallization zone 155 is generally at a temperature of about 210° C. or less, or about 100° C. to about 210° C., or about 150° C. to about 210° C., or about 180° C. to about 200° C. The pressure is generally in a range of about 0 MPa(g) (0 psig) to about 2.1 MPa(g) (300 psig), or 0 MPa(g) (0 psig) to about 2.8 MPa(g) (400 psig).

Additional crystallization vessels (not illustrated) similar to 135 and 155 may be added in series and the solid, volatile and non-volatile streams treated similarly to those generated in 135 and 155.

Solid product 165 is recovered from the second crystallization zone 155 (or from the first crystallization zone if there is only one).

The liquid portion with dissolved solids 170 is sent to the volatiles separation zone 145 where the liquid portion with dissolved solids 170 is separated into a volatile portion 175 and a non-volatile portion 180. The volatiles separation zone 145 could be the same vessel as one of the crystallization zones 135 or 155, or it could be a different vessel. Volatiles separation can be performed by one or more of distillation, evaporation, flash evaporation (achieved by reducing pressure), centrifugation or other separation step which removes the volatile portion of the liquid. The volatile portion 175 includes acetic acid, hydrobromic acid, water, and optionally ammonia, as well as methyl acetate and any other volatile side products that are generated in the oxidation. The non-volatile portion 180 includes ionic liquid, cobalt and manganese catalyst, dissolved reaction intermediates and products (which include toluic acid, toluamide, 4-CBA, terephthalic acid, and terephthalic acid monoamide).

Acetic acid can optionally be separated from the condensates of the volatile portion 175 by azeotropic distillation. However, the condensates in this process can be used without separation of water, if additional acetic acid is added to dilute the water, and recycled without detrimental effect on the oxidation reaction. If acetic acid is recycled, it is included as a portion of the make-up stream. The non-volatile portion 180 is also recycled. However, volatile portions of the recycled solvent had been removed from the non-volatile portion 180, so make-up acetic acid and/or HBr are added. Preferably, the amount of make-up components added is adjusted so that the proportions of acetic acid, water and HBr to ionic liquid in the recycle stream are the same as they were in the fresh mixture. The makeup components can include fresh volatile components 185, if needed, or the previously separated volatile components 175, or both.

In addition to makeup volatile components, ammonia and/or an ammonium compound, such as ammonium acetate, 190 can be added. The amount of ammonia and/or ammonium compound 200 added can be: 1) the same proportion as was added to the fresh mixture; 2) an amount equal to the amount of amide containing products that were generated in the reaction and removed when the solids were separated (in moles); or 3) the amount required to adjust the pH of the mixture to a desired pH between 3 and 7, where higher pH leads to lower 4-CBA content, but higher solvent burning. If ammonia is used instead of an ammonium compound, such as ammonium acetate, it is not made-up, but rather it is continuously bubbled through the oxidation zone 125 after recycle of the solvent. If the ammonium or ammonia component is not made-up before recycle, the levels of 4-CBA generated are considerably higher than if ammonia or ammonium acetate is made-up. Other bases, such as hydroxides, acetates, amines, or heterocyclic amines could also be used in place of ammonium acetate or ammonia.

Recycle solvent stream 195 is formed from the combination of non-volatile portion 180, volatile portion 175 with fresh components 185 and ammonia/ammonium compound 190.

Solvent 115 can be a combination of the recycle solvent stream 195 and fresh solvent stream 200.

In an alternate embodiment, instead of volatiles separation taking place after the last reaction or crystallization zone, the amount of acetic acid and water is reduced by flash evaporation in the last crystallization zone. Complete separation of volatile and non-volatile components is not necessary. The overhead volatiles removed in this way can be condensed downstream and recycled. After flash evaporation, the liquid is drained and treated like the non-volatile stream in FIG. 1. This modification has the advantage of saving utility cost for volatiles separation.

Figure 2:
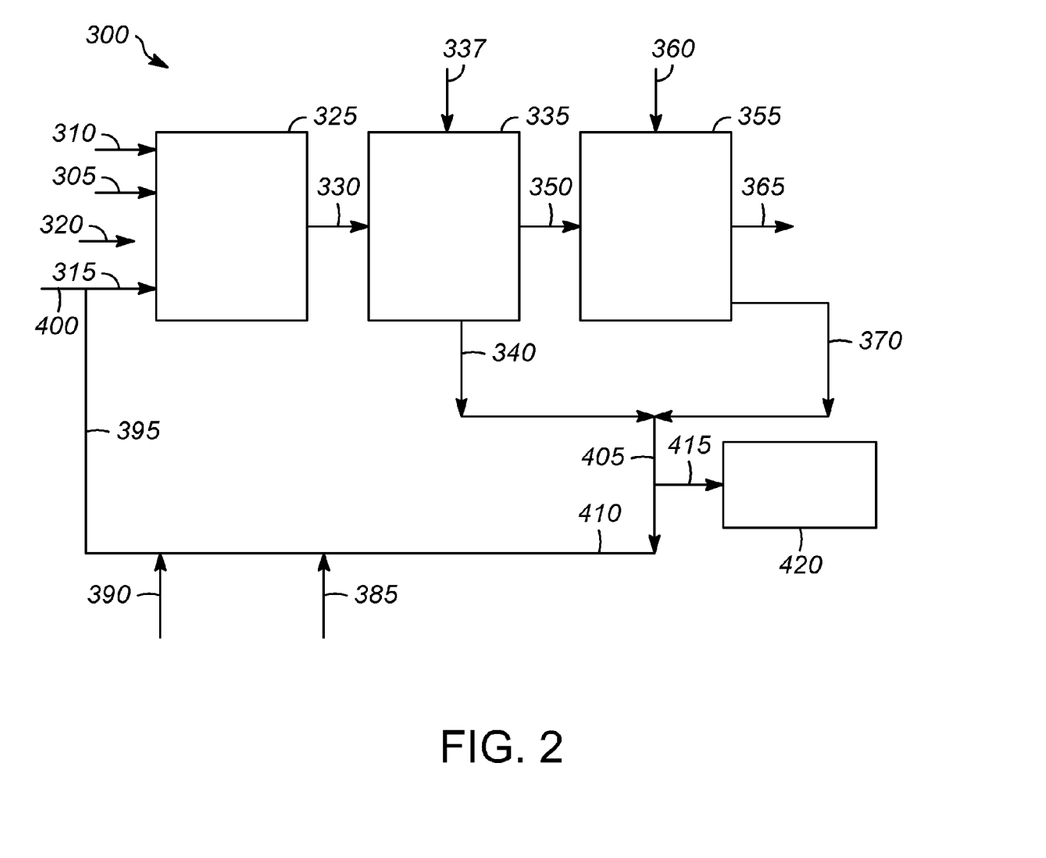
FIG. 2 is an illustration of another embodiment of an oxidation process to produce aromatic carboxylic acids including solvent recycle.

Another embodiment of the recycle process 300 is illustrated in FIG. 2. Para-xylene 305, and oxidant 310, solvent 315, and optionally ammonia or an ammonium source 320 are introduced into oxidation reaction zone 325 where the para-xylene 305 is oxidized to terephthalic acid.

The effluent 330 from the oxidation zone 325 is sent to a first crystallization zone 335. Crystallization is initiated by lowering the temperature in the first crystallization zone 335 or adding a crystallization solvent 337. During or after this crystallization step, some of the liquid portion 340 can be removed and recycled to the oxidation zone 325. Additional oxidation can also occur in the first crystallization zone 335, if desired.

The effluent 350 from the first crystallization zone 335 is sent to a second crystallization zone 355 where a second crystallization solvent 360 is added. The conditions in the second crystallization zone are similar to those of the first crystallization zone.

Alternatively, the crystallization solvent 360 can be added in the first crystallization zone 335, if desired.

Solid product 365 is recovered from the second crystallization zone 355 (or the first if there is only one).

The liquid portion with dissolved solids 370 is combined with the liquid portion 340 from the first crystallization zone 335 to form stream 405. The difference between this embodiment and that shown in FIG. 1 is that the volatile and non-volatile components are not separated. Stream 405 includes acetic acid, hydrobromic acid, and water, as well as methyl acetate and any other volatile side products that are generated in the oxidation, ionic liquid, cobalt and manganese catalyst, dissolved reaction intermediates and products (which include toluic acid, toluamide, 4-CBA, terephthalic acid, and terephthalic acid monoamide).

The liquid portion is optionally analyzed after solid-liquid separation to determine acid content and water content. The ionic liquid content can be determined by liquid chromatography, viscosity, conductivity, NMR, or density. The acid content can be determined by KOH titration, pH measurement or similar analysis. The water content can be determined by Karl-Fisher titration, infrared spectroscopy, or other known methods to determine water content.

Some of the liquid is recycled 410 as is, while some of the liquid 415 is sent for separation of volatile from non-volatile components in volatile separation zone 420, after which ionic liquid can be recovered. Since some portion acetic acid and HBr are invariably lost in the oxidation reaction (to oxidation, vent gasses, or other reactions), these components need to be made-up by adding volatile components 385, such as acetic acid and HBr, to the recycle stream 410. Additionally, this make-up of acetic acid serves to dilute the water that was generated in the oxidation. Ammonium acetate or ammonia 390 can be added into the recycle stream 410. The amount of make-up components 385 and 390 added to the recycle stream and the amount of recycle stream 395 mixed with fresh solvent 400 is controlled based on the analysis of the recovered liquid portions from the crystallizers (340 and 370). Alternatively, if analysis is not carried out, then these amounts are controlled to obtain the desired reaction rates and selectivities in the oxidation zone 325. This flow scheme is limited by the buildup of water in the recycle solvent 395. Unless sufficient acetic acid is added to dilute the water, the high water content will begin to attenuate the para-xylene oxidation reaction. If needed, a zone in which acetic acid and water are separated or in which water is removed by drying the stream can be added. Alternatively, water could be removed from the recycle stream by another means, such as adsorption on a drying agent such as magnesium sulfate or molecular sieves, or by azeotropic distillation to separate water and acetic acid. Alternatively, water and acetic acid are removed from the overhead of any of the vessels and acetic acid is replaced as necessary in make-up stream 385.

Recycle solvent stream 395 is formed from the stream 410 with fresh components 385 and ammonia/ammonium compound 390, Solvent 315 can be a combination of the recycle solvent stream 395 and fresh solvent stream 400.

Figure 3:
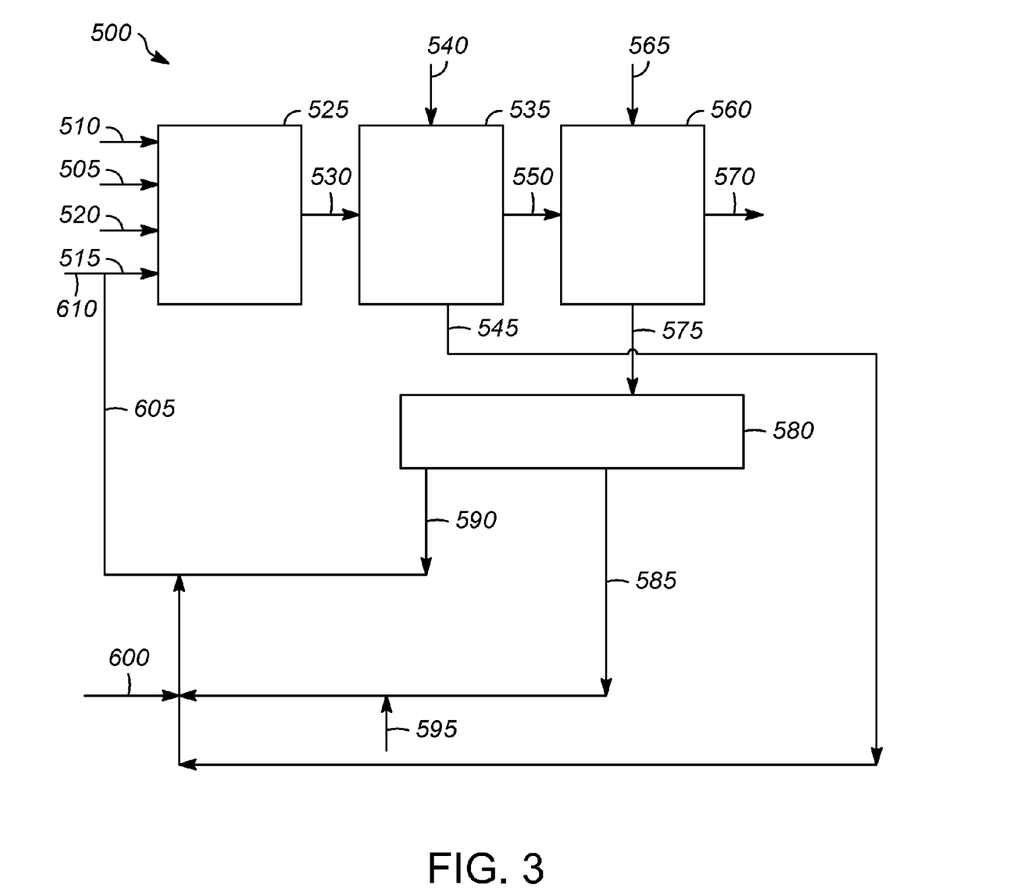
FIG. 3 is an illustration of another embodiment of an oxidation process to produce aromatic carboxylic acids including solvent recycle.

Another embodiment of a recycle process is shown in FIG. 3. The process is similar to the process FIG. 1, but it also includes a process loop for hydrolyzing amide containing products such as toluamide and terephthalic acid monoamide.

Para-xylene 505, and oxidant 510, solvent 515, and optionally ammonia or an ammonium source 520 are introduced into oxidation reaction zone 525 where the para-xylene 505 is oxidized to terephthalic acid.

The effluent 530 from the oxidation zone 525 is sent to a hydrolysis zone 535 for hydrolysis of the toluamide and terephthalic acid monoamide generated from the reaction of toluic acid and terephthalic acid with ammonia. In order to hydrolyze these products, water and/or acetic acid 540 is added. The temperature of the hydrolysis zone 535 is generally the same temperature as the oxidation zone 525 or less than 15° C. degrees less than the temperature of the oxidation zone 525. The hydrolysis zone 525 is generally at a temperature of about 150° C. to about 230° C., or about 180° C. to about 220° C., or about 200° C. to about 215° C. The pressure is chosen such that acetic acid and water remain in the liquid phase at the hydrolysis temperature, generally in a range of about 0.25 MPa(g) (40 psig) to about 2.1 MPa(g) (300 psig), or 0.65 MPa(g) (95 psig) to about 2.8 MPa(g) (400 psig). This process generates a mixture containing terephthalic acid which will begin to crystallize due to the lower solubility of terephthalic acid after addition of acetic acid and/or water. If acetic acid is used as the hydrolyzing agent, the mother liquor from this initial hydrolysis and crystallization contains mostly acetic acid with dissolved ammonia as well as ionic liquid and reaction intermediates and products.

The water and/or acetic acid can be added either directly after reaction, during crystallization, or in a post-treatment step (see e.g., U.S. Application Serial No. PCT/US14/57658, entitled PROCESS FOR REMOVING AMIDE IMPURITIES IN AROMATIC CARBOXYLIC ACIDS, filed on even date herewith, which is incorporated herein by reference). Desirably, the hydrolysis is conducted on dissolved terephthalic acid and terephthalic acid monoamide products directly following reaction either in the same vessel or in a subsequent vessel, in order to avoid utility costs associated with reheating the crystallized terephthalic acid.

The mother liquor 545 from the hydrolysis zone 535 is recycled as part of the makeup ammonium or ammonium acetate. Following the initial hydrolysis step, the effluent 550 from the hydrolysis zone is sent to a crystallization zone 560 where additional crystallization takes place by lowering the temperature, adding a crystallization solvent 565, or both. The temperature of the crystallization zone 560 is generally at least 10° C., or at least 20° C. less, than the temperature of the hydrolysis zone 535. The crystallization zone 560 is generally at a temperature of about 220° C. or less, or about 100° C. to about 220° C., or about 150° C. to about 220° C., or about 180° C. to about 200° C. The pressure is generally in a range of about 0 MPa(g) (0 psig) to about 2.1 MPa(g) (300 psig), or 0 MPa(g) (0 psig) to about 2.8 MPa(g) (400 psig).

Solid product 570 can be recovered from the second crystallization zone 560 (or the first if there is only one).

As in FIG. 1, the mother liquor 575 from the crystallization zone 560 is sent to a separation zone 580, which may or may not be a the same as crystallization zone 560, where it is subjected to flash evaporation or other process to separate the volatile portion 585 and non-volatile portion 590. Makeup volatiles 595 can be added to volatile portion 585 along with makeup ammonia/ammonium compound 600. This can be combined with non-volatile portion 590 to form recycle solvent stream 605.

Solvent 515 can be a combination of the recycle solvent stream 605 and fresh solvent stream 610.

In any of the embodiments, the amount of recycle compared to fresh solvent can vary. Adding higher amounts of fresh solvent has the disadvantage of higher cost, while adding less fresh solvent results in accumulation of reaction intermediates and impurities, such as polyaromatic compounds which could result in a colored final product.

In any of the flow schemes, the para-xylene to solvent ratio can be adjusted, as can the conversion of para-xylene and toluic acid in the oxidation reactor. Because the terephthalic acid product is much more soluble in ionic liquid mixtures than in conventional acetic acid mixture (e.g., about 7 g terephthalic acid/100 g solvent at 215° C. for one particular solvent composition), the products will remain entirely in the liquid phase unless conversion to terephthalic acid times the initial p-xylene to solvent ratio is greater than 7%. For example, if the amount of p-xylene at the reactor inlet is 10 wt % of the total feed (including solvent), then 70% conversion to terephthalic acid can be obtained before crystallization occurs.

The process may be practiced in laboratory scale experiments through full scale commercial operations. The process may be operated in batch, continuous, or semi-continuous mode. The contacting step can take place in various ways. The order of addition of the components (e.g., alkyl-aromatic compound, solvent, bromine source, catalyst, and oxidizing agent) is not critical. For example, the components can be added individually, or two or more components may be combined or mixed before being combined or mixed with other components. Individual process steps may be operated continuously and/or intermittently as needed for a given embodiment, e.g., based on the quantities and properties of the streams to be processed in such steps.

As used herein, the term "zone" can refer to one or more equipment items and/or one or more sub-zones. Equipment items may include, for example, one or more vessels, heaters, separators, exchangers, conduits, pumps, compressors, and controllers. Additionally, an equipment item can further include one or more zones or sub-zones. The solids separation, and/or contaminant extraction process or step may be conducted in a similar manner and with similar equipment as is used to conduct other solid-liquid wash and separation operations. Suitable equipment for solids separation includes, for example, filters, mixers, stirred tanks, settlers, centrifuges, cyclones, decanters, and augers. Suitable equipment for contaminant removal from liquid streams includes columns with trays, packing, rotating discs or plates, distillation columns, and vacuum distillation vessels.

Example 1

In one example, 20 g para-xylene was oxidized in a mixture of 50 g acetic acid, 20 g BMImBr, 10 g BMImOAc, 20 g ammonium acetate, and 0.4 g water with catalyst composed of 0.8 g Cobalt(II) acetate tetrahydrate, 0.6 g manganese(II) acetate and 0.4 g HBr. The reaction took place at 215° C. for three hours in semi-batch mode with continuous flow of air at 2500 sccm, and the temperature was maintained for the duration. After replacing air with nitrogen and cooling to room temperature to achieve crystallization, the product was filtered to remove solid reaction products. Note that room temperature filtration does not separate toluic acid from terephthalic acid, although filtration above 180° C. would. The solids were washed 3 times with room temperature water and then stirred in water at 80° C. for 30 min and filtered hot. The solid reaction products produced in this way (seven repetitions) had an average 4-CBA content of 19.7 ppm, an average toluic acid content of 2475 ppm, and an average terephthalic acid to terephthalic acid monoamide ratio of 4.37.

The used ionic liquid, generated as described above, was then subjected to vacuum distillation with centrifugation to remove volatile components at 72° C. for 14-20 hours utilizing a staged vacuum method. The non-volatile residue, which contained ionic liquid, catalyst, and reaction intermediates, was combined with the non-volatile components from other identical runs. This recycled ionic liquid was combined with fresh acetic acid and ammonium acetate in a 5:2:3 weight ratio of acetic acid to ammonium acetate to recycled ionic liquid. To this mixture, 0.4 g water and 0.4 g HBr were added to obtain a mixture similar to the starting mixture but with recycled ionic liquid. This solvent and catalyst were used for an oxidation reaction starting with 20 g para-xylene, run under similar conditions to the initial oxidation reaction in fresh ionic liquid.

The solid products from this procedure contained 0 ppm of 4-CBA, 0 ppm toluic acid or toluamide, and a terephthalic acid to terephthalic acid monoamide ratio of 3.1. The process was repeated, and the solid products contained 34 ppm of 4-CBA, 4039 ppm toluic acid or toluamide, and the terephthalic acid to terephthalic acid monoamide ratio was 3.9. As a comparison, when no ammonium acetate was added to the recycled ionic liquid (the only ammonium was what remained after the first reaction and the vacuum distillation step), the resulting level of 4-CBA was 6811 ppm, and there was 6173 ppm of toluic acid.

The same procedure used to produce the recycled ionic liquid and make-up components was used for a second generation of recycled ionic liquid and a third recycle. The same procedure was followed as was used to generate the first recycled ionic liquid. This second recycle resulted in 188 ppm 4-CBA, 2680 ppm toluic acid, and 0 ppm toluamide in the final solid products. The third recycle resulted in 248 ppm 4-CBA, 2503 ppm toluic acid, and 193 ppm toluamide.

The amount of $CO_x$ ($CO_2$+CO) generated was monitored by infrared using an MKS infrared analyzer in several of the oxidation runs. In two runs using fresh ionic liquid, 33 and 34 g $CO_x$ were generated in the three hour run. In a run using once recycled ionic liquid, 25 g $CO_x$ was generated. In one run using twice recycled ionic liquid, 27 g of $CO_x$ was generated. In the run using three times recycled ionic liquid, 11 g $CO_x$ was generated. The amount of $CO_x$ appears to be reduced with each recycle run. Although not wishing to be bound by theory, it is believed that this is likely due to a higher concentration of hydroperoxide-forming radicals, stabilization of the solvent towards deep oxidation, or metal loss in each successive recycle, since no effort was made to remove un-reacted products from the filtered liquid phase or to add make-up metals before it was recycled.

Example 2

In this example, the experiment was similar to Example 1, but with the following two differences. First, the ionic liquid portion in each recycle was 85 wt % ionic liquid from the previous cycle and 15 wt % fresh ionic liquid, where the fresh ionic liquid consisted of 33.3 wt % BMImOAc and 66.7 wt % BMImBr—which was the same BMImOAc to BMImBr ratio used in the oxidation using fresh ionic liquid. The other components of the mixture were the same. Second, this series was run on a different reactor in which there was less external control over heating. This resulted in loss of heat after the reaction exotherm was complete, so the final 1-2 hours of reaction were conducted at 211-214° C. rather than 215° C. This seems to have resulted in lower conversion of intermediates. The results from these recycle experiments are shown in Table 2. In these tests, the level of 4-CBA remained below 900 ppm through three cycles; however, the 4-CBA levels after the first cycle were already high due to the lower temperature. Also in addition, $CO_x$ formation resulting from solvent oxidation dramatically decreased with each cycle. In this set of experiments, the metal catalyst was made up in each cycle to ensure that this effect was not due to catalyst loss.

TABLE 1

No Makeup of Ionic Liquid in Recycle

| Starting material | Sample | Solid components | | | | | | |
|---|---|---|---|---|---|---|---|---|
| | | p-toluamide ppm | p-toluic acid ppm | 4-CBA ppm | % TA-ma | % TA | benzoic acid ppm | TA/TAMA |
| Fresh solvent | 34593-2 | not analyzed | 310 | 0 | 18.3% | 77.3% | 0 | 4.23 |
| | 34924-3 | not analyzed | 196 | 0 | 13.5% | 79.4% | 0 | 5.88 |
| | 34924-15 | 5797 | 11051 | 49.1 | 25.0% | 76.1% | 3733 | 3.04 |
| | 34924-9 | 1106 | 4852 | 23.5 | 18.4% | 75.6% | 2116 | 4.11 |
| | 34924-6 | not analyzed | 160 | 0 | 16.5% | 77.7% | 3830 | 4.69 |
| | 34924-5 | not analyzed | 658 | 55.8 | 17.9% | 76.1% | 0 | 4.24 |
| | 34924-4 | not analyzed | 94 | 9.3 | 17.2% | 76.2% | 0 | 4.42 |
| | mean | 3452 | 2475 | 19.7 | 18% | 77% | 1383 | 4.37 |
| | σ | 3317 | 4152 | 24 | 3.5% | 1.3% | 1812 | 0.84 |
| 1st recycle Add ammonium acetate | 34593-54 | not analyzed | 0 | 0 | 23.8% | 74.4% | 0 | 3.13 |
| | 34924-10 | 4039 | 0 | 34.2 | 18.5% | 71.7% | 2022 | 3.87 |
| | mean | 4039 | 0 | 17 | 21% | 73% | 1011 | 3.50 |
| | σ | n/a | 0 | 24 | 3.7% | 1.9% | 1430 | 0.52 |
| 2nd recycle | 34924-13 | 0 | 2680 | 188 | 18.1% | 70.0% | 2552 | 3.87 |
| 3rd recycle | 34924-17 | 193 | 2503 | 248 | 31.0% | 74.6% | 0 | 2.40 |
| Fresh solvent no ammonium acetate | 34926-3 | 0 | 2295 | 20278 | 3.0% | 86.3% | 502 | 28.96 |
| 1st recycle no added ammonium acetate | 34924-8 | 0 | 6173 | 6811 | 15.5% | 80.6% | 3856 | 5.21 |

| Starting material | Sample | Solid components | | Liquid | | | |
|---|---|---|---|---|---|---|---|
| | | Toluamide/ total toluates | % Total terephthalates | Total toluates ppm | Acid number (mg KOH titrant/g sample) | H2O (wt %) | Reactor Effluent COx (g) |
| Fresh solvent | 34593-2 | | 95.6% | 310 | 310 | 18.82% | not measured |
| | 34924-3 | | 92.9% | 196 | 262 | 14.71% | not measured |
| | 34924-15 | 0.34 | 101.1% | 16848 | 284 | 5.44% | 33.05 |
| | 34924-9 | 0.19 | 93.9% | 5959 | 310 | 19.02% | 34.02 |
| | 34924-6 | | 94.2% | 160 | 301 | 15.50% | not measured |
| | 34924-5 | | 94.0% | 658 | 211 | 12.37% | not measured |
| | 34924-4 | | 93.5% | 94 | 315 | 20.68% | not measured |
| | mean | 0.26 | 95% | 3461 | 285 | 15% | 34 |

TABLE 1-continued

No Makeup of Ionic Liquid in Recycle

|   | σ | 0.11 | 2.8% | 6273 | 37 | 5% | 1 |
|---|---|---|---|---|---|---|---|
| 1st recycle Add ammonium acetate | 34593-54 |  | 98.2% | 0 | 410 | 20.78 | n/a |
|  | 34924-10 | 1.00 | 90.2% | 4039 | 371 | 16.47 | 24.72 |
|  | mean | 1.00 | 94% | 2020 | 391 | 19 | 25 |
|  | σ | n/a | 5.6% | 2856 | 28 | 3 | n/a |
| 2nd recycle | 34924-13 | 0.00 | 88.1% | 2680 | 374 | 20.19 | 27.14 |
| 3rd recycle | 34924-17 | 0.07 | 105.6% | 2696 | 453 | 13.05 | 10.99 |
| Fresh solvent no ammonium acetate | 34926-3 | 0.00 | 89.3% | 2295 | 499 | 15.4% | not measured |
| 1st recycle no added ammonium acetate | 34924-8 | 0.00 | 96.1% | 6173 | 422 | 11.58 | not measured |

TABLE 2

Recycle with Ionic Liquid Makeup

| Test | 34924-23 | 34924-31 | 34924-33 | 34924-34 | 34924-29 | 34924-38 | 34924-40 | 34924-42 | Fresh Average | 1$^{st}$ Recycle Average |
|---|---|---|---|---|---|---|---|---|---|---|
| Type | Fresh Ox | Fresh Ox | Fresh Ox | Fresh Ox | Fresh Ox | Recycle | Recycle | 2nd Recycle |  |  |
| Solid products ppm |  |  |  |  |  |  |  |  |  |  |
| 4-CBA | 89.545 | 135.51 | 525.375 | 2246.06 | 89.545 | 683.56 | 823.235 | 723.55 | 617.2 | 753.4 |
| TA | 647856.3 | 742486.5 | 652200 | 626179 | 647856.3 | 633460.5 | 589306.1 | 626034.8 | 663315.6 | 611383.3 |
| TA-ma | 208800.4 | 274544.5 | 299962 | 312061 | 208800.4 | 304379.7 | 295813.7 | 372809.3 | 260833.7 | 300096.7 |
| p-toluic acid | 753.865 | 1638.77 | 9422.47 | 37484.92 | 753.865 | 11513.18 | 10414.53 | 9691.365 | 10010.8 | 10963.9 |
| p-toluamide | 241.405 | 715.925 | 2012.13 | 5527.21 | 241.405 | 1903.535 | 1489.47 | 1434.815 | 1747.6 | 1696.5 |
| COx (g) | 19.41 | 7.84 | 25.47 | not measured | not measured | 8.07 | 7.51 | 6.73 | 17.6 | 7.8 |

Example 3

In one set of examples, acetic acid, 1-butyl-3-methylimidazolium (BMIm) acetate, BMIm bromide, ammonium acetate, water and terephthalic acid were combined in an autoclave, heated to a given temperature and pressurized to 400 psig under nitrogen. After at least one hour, the liquid portion of the mixture was then sampled through a dipleg, which had a 10-micron titanium filter affixed to its end, into a 6 mL titanium pressure vessel. This filter is intended to exclude solid material from the sample. This process was then repeated at higher temperatures. The samples were cooled, collected, and analyzed by HPLC. The results (Table 3) show that at higher temperatures and in compositions that contain higher amounts of ionic liquid components, the composition contains more terephthalic acid in the liquid (solution) phase, and less in the solid phase (deduced by difference). Acetic acid is included in Table 3 as a comparative example.

A similar experiment was conducted at atmospheric pressure but using heptanoic acid instead of acetic acid. The amount of terephthalic acid in the liquid phase in this composition was similarly high (see Table 3).

TABLE 3

| | Example | | | | | | | |
|---|---|---|---|---|---|---|---|---|
| | 3A | | 3B | | 3C | | 3D | |
| Composition of mixture (grams) | | | | | | | | |
| | Acetic Acid | 220 | Acetic Acid | 110 | Acetic Acid | 188.33 | Acetic Acid | 146.67 |
| | BMImOAc | — | BMImOAc | 22 | BMImOAc | 7.33 | BMImOAc | 14.67 |
| | BMImBr | — | BMImBr | 44 | BMImBr | 14.67 | BMImBr | 29.33 |
| | NH4OAc | — | NH4OAc | 44 | NH4OAc | 14.67 | NH4OAc | 29.33 |
| | H2O | 22 | H2O | 11.7 | H2O | 5.21 | H2O | 5.21 |
| | Terephthalic acid (TA) | 20 | TA | 20 | TA | 20.00 | TA | 20.00 |
| Temperature and solubility of TA | | | | | | | | |
| Temp [C.] | g TA soluble in liquid/ 100 g mixture | Temp [C.] | g TA soluble in liquid/ 100 g mixture | Temp [C.] | g TA soluble in liquid/ 100 g mixture | Temp [C.] | g TA soluble in liquid/ 100 g mixture | |
| 25 | 0.01 | 25 | 0.15 | 25 | 0.02 | 25 | 0.03 | |
| 25 | 0.07 | 161 | 2.17 | 185 | 2.80 | 185 | 2.96 | |
| 150 | 0.62 | 169 | 2.95 | 200 | 2.86 | 199 | 4.15 | |
| 151 | 0.51 | 180 | 2.85 | 215 | 3.97 | 216 | 5.61 | |
| 151 | 0.49 | 190 | 4.43 | | | | | |
| 180 | 0.83 | 200 | 6.09 | | | | | |
| 180 | 1.13 | 201 | 5.73 | | | | | |
| 200 | 1.95 | 202 | 6.32 | | | | | |
| | | 205 | 6.71 | | | | | |
| | | 213 | 5.96 | | | | | |
| | | 215 | 7.15 | | | | | |
| | | 218 | 6.86 | | | | | |

| | Example | | | | | |
|---|---|---|---|---|---|---|
| | 3E | | 3F | | 3G | |
| Composition of mixture (grams) | | | | | | |
| | Acetic Acid | 88.00 | Heptanoic Acid | 20 | Heptanoic Acid | 9 |
| | BMImOAc | 26.40 | BMImOAc | — | BMImOAc | 1.5 |
| | BMImBr | 52.80 | BMImBr | — | BMImBr | 3 |
| | NH4OAc | 52.80 | NH4OAc | — | NH4OAc | — |
| | H2O | 5.21 | H2O | 2 | H2O | — |
| | TA | 20.00 | TA | 4 | TA | 3.9 |
| Temperature and solubility of TA | | | | | | |
| Temp [C.] | Temp [C.] | g TA soluble in liquid/ 100 g mixture | Temp [C.] | g TA soluble in liquid/ 100 g mixture | Temp [C.] | g TA soluble in liquid/ 100 g mixture |
| 25 | 25 | 0.29 | 25 | 0.00852 | 25 | 1.46 |
| 25 | 185 | 4.24 | 175 | 1.28 | 185 | 4.38 |
| 150 | 200 | 6.29 | 181 | 0.373 | 200 | 5.64 |
| 151 | 215 | 6.40 | 200 | 0.409 | 215 | 5.52 |
| 151 | | | | | | |
| 180 | | | | | | |
| 180 | | | | | | |
| 200 | | | | | | |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for oxidizing an alkyl aromatic compound comprising:
contacting the alkyl aromatic compound, a first solvent comprising an ionic liquid and a carboxylic acid, a bromine source, a catalyst, and an oxidizing agent in a reaction zone under oxidizing conditions to produce an oxidation product comprising aromatic carboxylic acid, and at least one of dissolved unoxidized alkyl aromatic compound or dissolved partially oxidized alkyl aromatic compound, at least 25% of the aromatic carboxylic acid remaining in solution;
crystallizing at least a portion of the aromatic carboxylic acid in a crystallization zone to produce a solid product comprising a crystallized aromatic carboxylic acid and a mother liquor liquid comprising the first solvent, and the at least one of unoxidized alkyl aromatic compound or partially oxidized alkyl aromatic compound and optionally aromatic carboxylic acid in solution;
separating the solid product from the mother liquor liquid;
separating the mother liquor liquid into a volatile portion comprising one or more of the carboxylic acid, the bromine source, and water, and a nonvolatile portion aromatic compound or dissolved partially oxidized alkyl aromatic compound;
optionally introducing one or more of additional ionic liquid, additional carboxylic acid, additional bromine source, or additional ammonia or ammonium compound into the nonvolatile portion; and
recycling at least a portion of the nonvolatile portion to the first reaction zone.

2. The process of claim 1 wherein one or more of additional ionic liquid, additional carboxylic acid, additional bromine source, or additional ammonia or ammonium compound is introduced into the nonvolatile portion and wherein at least a portion of the additional carboxylic acid, or additional bromine source comprises the carboxylic acid or the bromine source from the volatile portion.

3. The process of claim 1 wherein separating the mother liquor liquid into the volatile portion and the nonvolatile portion occurs in the crystallization zone.

4. The process of claim 1 wherein crystallizing at least a portion of the aromatic carboxylic acid comprises introducing a crystallization solvent to the crystallization zone, the oxidation product having a lower solubility in the crystallization solvent than in the ionic liquid; and wherein the mother liquor further comprises the crystallization solvent, or lowering a temperature of the solution containing the oxidation product, or both.

5. The process of claim 4 wherein the crystallization solvent comprises a carboxylic acid, and wherein the carboxylic acid of the crystallization solvent is the same as the carboxylic acid of the first solvent.

6. The process of claim 5 further comprising:
separating the carboxylic acid of the crystallization solvent and the carboxylic acid of the first solvent from the volatile portion.

7. The process of claim 4 wherein the temperature is lowered before introducing the crystallization solvent.

8. The process of claim 4 wherein lowering the temperature of the solution containing the oxidation product occurs in a second crystallization zone positioned after the crystallization zone, and further comprising:
removing liquid from the second crystallization zone, wherein the liquid from the second crystallization zone comprises the first solvent, and the at least one of the unoxidized alkyl aromatic compound or the partially oxidized alkyl aromatic compound and optionally aromatic carboxylic acid in solution; and
recycling at least a portion of the liquid from second crystallization zone to the reaction zone.

9. The process of claim 8 further comprising separating the liquid from the second crystallization zone into a volatile portion and a nonvolatile portion.

10. The process of claim 1 further comprising:
oxidizing at least a portion of the unoxidized alkyl aromatic compound or partially oxidized alkyl aromatic compound in the crystallization zone.

11. The process of claim 1 wherein ammonia or an ammonium compound is contacted with the alkyl aromatic compound, the first solvent, the bromine source, the catalyst, and the oxidizing agent in the reaction zone.

12. The process of claim 11 wherein the oxidation product further comprises an amide compound, and further comprising:
hydrolyzing the amide compound with a second carboxylic acid, water, or both, to an ammonium compound or ammonia and an aromatic carboxylic acid.

13. The process of claim 12 wherein crystallizing at least a portion of the aromatic carboxylic acid comprises introducing a crystallization solvent to the crystallization zone, and wherein the crystallization solvent comprises a carboxylic acid, and wherein the carboxylic acid of the crystallization solvent is the same as the second carboxylic acid.

14. The process of claim 12 further comprising:
removing a portion of liquid after hydrolyzing the amide compound; and
recycling the hydrolyzed ammonium compound or ammonia to the reaction zone.

15. The process of claim 12 wherein hydrolyzing the amide product with the second carboxylic acid, water, or both to the ammonium compound or ammonia and an aromatic carboxylic acid occurs in the reaction zone.

16. The process of claim 1 further comprising:
dividing the mother liquor liquid into a first portion and a second portion
before separating the second portion into the volatile portion comprising one or more of the carboxylic acid, the bromine source, and water, and the nonvolatile portion comprising the ionic liquid, the catalyst, and the at least one of dissolved unoxidized alkyl aromatic compound or dissolved partially oxidized alkyl aromatic compound; and
recycling the first portion to the reaction zone.

17. The process of claim 16 further comprising:
recovering ionic liquid from the nonvolatile portion.

18. The process of claim 16 further comprising:
determining at least one of the ionic liquid content, the water content, or the acid content of the mother liquor liquid.

19. The process of claim 16 further comprising:
removing water from the first portion before recycling the first portion to the reaction zone.

20. The process of claim 1 wherein a weight ratio of the ionic liquid to the carboxylic acid in the first solvent is in a range of about 0.1:1 to about 10:1.

* * * * *